(12) United States Patent
Stone

(10) Patent No.: US 9,259,437 B2
(45) Date of Patent: Feb. 16, 2016

(54) SCLERAL LENS SOLUTION

(71) Applicant: SMM Ventures, LLC, Fort Worth, TX (US)

(72) Inventor: Ralph P Stone, Fort Worth, TX (US)

(73) Assignee: SMM Ventures, LLC, Ft. Worth, TX (US)

( * ) Notice: Subject to any disclaimer, the term of this patent is extended or adjusted under 35 U.S.C. 154(b) by 0 days.

(21) Appl. No.: 14/284,575

(22) Filed: May 22, 2014

(65) Prior Publication Data

US 2014/0348956 A1 Nov. 27, 2014

Related U.S. Application Data

(60) Provisional application No. 61/826,605, filed on May 23, 2013.

(51) Int. Cl.
| | | |
|---|---|---|
| *A61F 2/00* | (2006.01) | |
| *A61K 9/00* | (2006.01) | |
| *A61K 33/06* | (2006.01) | |
| *A61K 33/00* | (2006.01) | |

(52) U.S. Cl.
CPC ............... *A61K 33/06* (2013.01); *A61K 9/0048* (2013.01); *A61K 33/00* (2013.01); *A61K 9/0051* (2013.01)

(58) Field of Classification Search
None
See application file for complete search history.

(56) References Cited

U.S. PATENT DOCUMENTS

| | | | |
|---|---|---|---|
| 4,911,933 A | 3/1990 | Gilbard | |
| 5,578,578 A | 11/1996 | Hecht et al. | |
| 5,696,171 A * | 12/1997 | Rupp et al. | 514/700 |
| 6,024,954 A * | 2/2000 | Park et al. | 424/94.2 |
| 2009/0239775 A1 | 9/2009 | Collins et al. | |
| 2013/0188124 A1* | 7/2013 | Li et al. | 351/159.33 |

OTHER PUBLICATIONS

Foreign Communication From A Related Counterpart Application, PCT Application PCT/US2014/39117, International Search Report dated Sep. 4, 2014, 8 pages.
Foreign Communication From A Related Counterpart Application, PCT Application PCT/US2014/39117, Written Opinion dated Sep. 4, 2014, 4 pages.
Anderson, A., et al., "Comparison of Aqueous Humour and Serum Zinc Levels in Humans," British Journal of Ophathamology, 1987, vol. 71, pp. 212-214.
Araie, M., et al., "Effect of Calcium Ion Concentration on the Permeability of the Corneal Endothelium," Investigative Ophthamology & Visual Science, vol. 31, No. 10, Oct. 1990, pp. 2191-2193.
Araie, M., "Barrier Function of Corneal Endothelium and the Intraocular Irigating Solutions," Arch Ophthalmol, vol. 104, No. 3, Mar. 1986, pp. 435-438, Abstract.
Armitage, W.J., et al., "Effects of Osmotic Stress on Rabbitt Corneal Endothelium," Cryobiology, vol. 25, No. 5, Oct. 1988, pp. 425-439, Abstract.
Bachman, W., et al., "Essential Ions for Maintenance of the Corneal Epithelial Surface," Investigative Ophthamology & Visual Science, vol. 26, No. 11, Nov. 1985, pp. 1484-1488.
Bonanno, J.A., et al., "Identity and Regulation of Ion Transport Mechanisms in the Corneal Endothelium," Progress in Retinal and Eye Research, vol. 22, 2003, pp. 69-94.
"BSS ® (Balanced Salt Solution)," Alcon Insert for BSS, http://home.intekom.com/pharm/alcon/bss.html, Jan. 11, 2013, 1 page.
Edelhauser, H., "The Balance Between Corneal Transparency and Edema," Investigative Ophthamology & Visual Science, vol. 47, No. 5, May 2006, pp. 1755-1767, Abstract.
Edelhauser, H., et al., "Intraocular Irrigating Solutions. Their Effect on the Corneal Endothelium," Arch Ophthalmol, vol. 93, No. 8, Aug. 1975, pp. 648-657, Abstract.
Edelhauser, H., et al., "Osmotic Tolerance of Rabbit and Human Corneal Endothelium," Arch Ophthalmol, vol. 99, No. 7, Jul. 1981, pp. 1281-1287, Abstract.
Gonnering, R., et al., "The pH Tolerance of Rabbit and Human Corneal Endothelium," Investigative Ophthamology & Visual Science, vol., 18, No. 4, Apr. 1979, pp. 373-390.
Green, K., et al., "Tear Potassium Contributes to Maintenance of Corneal Thickness," Ophthalmic Research, vol. 24, No. 2, 1992, pp. 99-102, Abstract.
Huang, Y., et al., "Swelling Studies on the Cornea and Sclera: The Effects of pH and Ionic Strength," Biophysical Journal, vol. 77, Sep. 1999, pp. 1655-1665.
Kangas, T.A., et al., "Loss of Stromal Glycosaminoglycans During Corneal Edema," Investigative Ophthamology & Visual Science, vol. 31, No. 10, Oct. 1990; pp. 1994-2002, Abstract.
Luo, L., et al., "Hyperosmolarity-Induced Apoptosis in Human Corneal Epithelial Cells is Medicated by Cytochrome c and MAPK Pathways," Cornea, vol. 26, No. 4, May 2007, pp. 452-460.
Nuyts, R.M., et al., "Toxic Effects of Detergents on the Corneal Endothelium," Arch Ophthalmol, vol. 108, No. 8, 1990, pp. 1158-1162, Abstract.
Richards, B., "How to Insert a Scleral Lens," www.ehow_7645888_insert-sceral-lens.html, Jan. 21, 2013, 1 page.
Schrage, N., et al., "Do Different Osmolar Solutions Change the Epithelial Surface of the Healthy Rabbit Cornea?," Graefe's Archive for Clinical and Experimental Ophthalmology, Springer-Verlag 2004, 12 pages.
Weekers, J.F., et al., The Effects of Intraocular Irrigating Solutions on the Human Corneal Endothelium (author's translation)], J Fr Ophtalmol, vol. 1, No. 11; Nov. 1978, pp. 643-648.
Wilson, G., "The Effect of Osmolality on the Shedding Rate of the Corneal Epithelium," Cornea, vol. 15, No. 3, May 1996, pp. 240-244, Abstract.

* cited by examiner

*Primary Examiner* — Susan Tran

(57) ABSTRACT

A scleral lens solution comprising an aqueous mixture that includes sodium, potassium, calcium and magnesium cations and a pH in a range from about 6.5 to about 8.7.

22 Claims, 3 Drawing Sheets

SCLERAL LENS SOLUTION

CROSS-REFERENCE TO PROVISIONAL APPLICATION

This application claims the benefit of U.S. Provisional Application No. 61/826,605, filed by Ralph P. Stone on May 23, 2013, entitled, "SCLERA LENS SOLUTION," which is fully incorporated herein by reference herein in its entirety.

TECHNICAL FIELD

This application is directed, in general, to scleral lens solutions and to methods of preparing and using such solutions.

BACKGROUND

Scleral lenses are a special type of rigid contact lenses used to vault over the cornea, leaving a space between the contact lens and the cornea. Scleral lenses are often used for patients with corneal problems such as keratoconnus, irregular astigmatism, surgically induced corneal irregularities, or persistent corneal defects. These patients often already have diseased or compromised corneas and therefore wearing of contact lenses need to minimize the potential for additional damage and patient discomfort. To provide acceptable vision, a solution is often used to provide a liquid interface that fills the void between the lens and the cornea.

SUMMARY

The present disclosure provides in one embodiment, a scleral lens solution that comprises an aqueous mixture including sodium, potassium, calcium and magnesium cations and a pH in a range from about 6.5 to about 8.7.

In some such embodiments, the aqueous mixture can be an artificial preservative-free pH buffered solution that can include at least one of phosphate buffer or borate buffer. In some such embodiments, the aqueous mixture can be free of a strong divalent metal ions chelator. In some such embodiments, the aqueous mixture can have an osmolality in a range of about 300 to about 450 mosm.

In some such embodiments, the aqueous mixture can include a sodium concentration in a range of about 120 to about 170 mM. In some such embodiments, the aqueous mixture can include a potassium concentration in a range of about 6 to about mM. In some such embodiments, the aqueous mixture can include a calcium concentration in a range of about 0.5 to about 2.5 mM. In some such embodiments, the aqueous mixture can include a magnesium concentration in a range of about 0.3 to about 1.7 mM. In some such embodiments, the aqueous mixture can include have an osmolality in a range of about 300 to about 450 mosm and can include any combination of one or more of sodium, potassium, calcium or magnesium with the above concentration ranges.

In some such embodiments the aqueous mixture can include sodium and potassium with a mole ratio in a range of about 5.0:1 to about 6.5:1. In some such embodiments the aqueous mixture can include calcium and magnesium with a mole ratio in a range of about 1:1 to about 2:1.

Any such embodiments can further include at least one of zinc or copper. In some such embodiments the aqueous mixture has cations that consist essentially of sodium, potassium, calcium, magnesium, zinc and copper. Any such embodiments can further include includes one or more monosaccharide. In some such embodiments, a total concentration of the monosaccharides in the aqueous solution is in a range of about 10 to about 100 mg/liter. Any such embodiments can further include one or more demulcent. Any such embodiments can further include includes one or more reducing agent.

Still another embodiment of the disclosure is a method of preparing a scleral lens solution that comprises providing a volume of liquid water, adding sodium, potassium, calcium and magnesium cations to the volume of water to form a solution and adjusting the pH of the solution in a range from about 6.5 to about 8.7.

Still another embodiment of the disclosure is a method using a scleral lens solution. The method comprises providing a scleral lens solution that comprises an aqueous mixture including sodium, potassium, calcium and magnesium cations and a pH in a range from about 6.5 to about 8.7. The method further comprises contacting a scleral lens with the scleral lens solution.

BRIEF DESCRIPTION OF DRAWINGS

For a more complete understanding of the present disclosure, reference is now made to the following detailed description taken in conjunction with the accompanying FIGUREs. Reference is now made to the following descriptions taken in conjunction with the accompanying drawings, in which.

DETAILED DESCRIPTION

Figure 1:
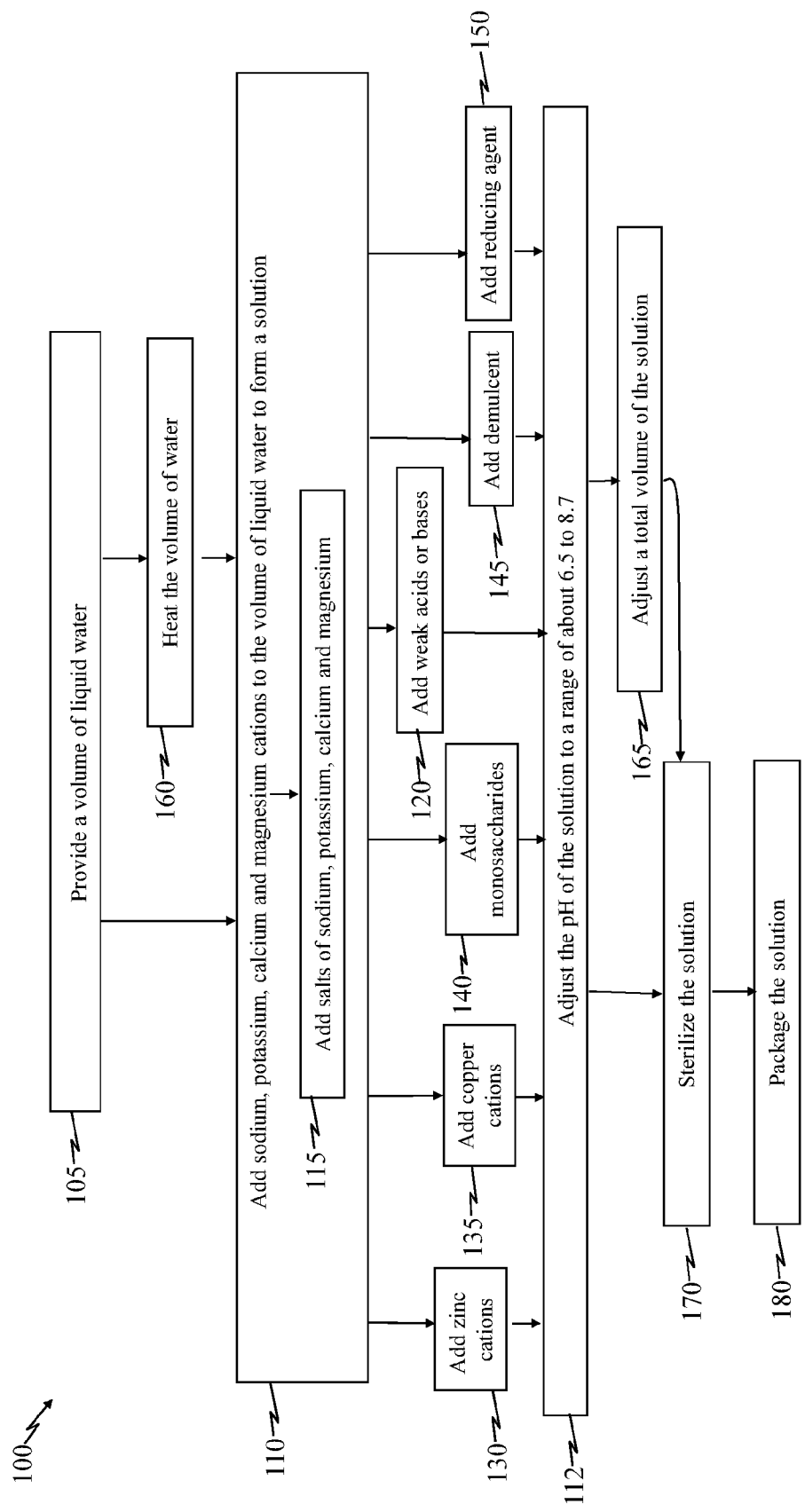
FIG. 1 illustrates by flow diagram, selected aspects of an example method of preparing a scleral lens solution according to the principles of the present disclosure.

Embodiments of the present disclosure benefit from the recognition that the composition of certain commercially available contact lens solutions are not optimal, and in some cases may be detrimental, to corneal health when used as a scleral lens solutions, e.g., any or all of insertion, rinse or re-wetting solutions commonly used for contact lenses.

Consider for instance, conventional contact lens solutions, e.g., insertion solutions used with hard and soft lenses designed for vision correction, e.g., due to myopia. These conventional contact lens solutions were designed under the expectation that the solution is exchanged with the tear film on a time scale ranging from a few minutes to 30 minutes. In contrast, scleral lens solutions used as insertion solutions are expected to remain under lens for an extended period, e.g., for several hours throughout daily wear, with substantially no exchange with the tear film during this period. Consequently, there are concerns that the healing of a defective cornea under the scleral lens will be compromised or possibly additional damaged, by long periods of exposure to preservative chemicals present in such conventional contact lens solutions. In view of these concerns, some doctors have resorted to recommending the use of sterile saline, e.g., indicated for inhalation therapy, as a scleral lens solution (e.g., an insertion solution). Problems with such sterile saline solutions, however, can include edema formation in the corneal tissue or other ocular tissue under the lens, resulting in poor (e.g., hazy) vision while wearing the lens, delayed healing, or possible additional new tissue damage.

Embodiments of the present disclosure address the long-felt need for a scleral lens-specific solution (e.g., for lens insertion), by providing a preservative-free buffered solution containing a plurality of ions at concentrations ranges present in ocular tissues. While not limiting the scope of the disclosure by theoretical considerations, it is believed that such a scleral lens solution facilitates clear vision while avoiding the potential health concerns associated with exposing diseased or compromised corneal tissue to conventional contact lens solutions.

One embodiment of the disclosure is a scleral lenses solution. Embodiments of the scleral lenses solution can comprise an aqueous mixture that includes sodium, potassium, calcium and magnesium cations and a pH in a range from about 6.5 to about 8.7.

The presence of these four cations facilitates providing a scleral lens solution that presents the corneal and other ocular tissue under the lens with a cation environment similar to that of natural tears. To reduce edema formation in the corneal or other ocular tissue, the ratio of these cations and their total concentrations are designed to provide a solution equal to or slightly higher in osmotic pressure than the corneal tissue and/or the tears of a normal healthy individual (referred to herein as "normal tears").

The beneficial presence of the divalent ions in the scleral lens solution, such as calcium and magnesium, is surprising, because these divalent ions are generally avoided in conventional contact lens solutions. Calcium and magnesium are avoided in conventional contact lens solutions out of concern that solutions containing these divalent cations will tend to form precipitates, e.g., with lipids and protein present in the tear film. The formation of calcium and/or magnesium-containing precipitates, often referred to as lens calculi or jelly bumps, are known to cause spoliation of the contact lens.

In the present embodiments, however, the presence of calcium and magnesium in scleral lens solutions to promote corneal health is considered more important than the risk of lens spoliation due to precipitate formation. Because scleral lens solutions are in very slow exchange with the tear film, the likelihood of such precipitate formation is greatly reduced when wearing of scleral lenses. Moreover, because the scleral lens is typically removed daily, normal cleaning procedures can be used to reduce the build-up of such precipitates. An additional benefit to providing scleral lens solutions that include calcium and magnesium is that there is no longer a need to include strong divalent metal ion chelators, such as ethylenediaminetetraacetic acid (EDTA) or similar chelators in the solution. That is, embodiments of the scleral lens solutions can be free of strong divalent metal ions chelators, to facilitate the free ion concentrations of calcium and magnesium being substantially at physiologic levels. In some embodiments, a divalent metal ions chelator is considered a strong chelator if it has a stability constant with respect to calcium and magnesium in the scleral lens solution of at least about 9 and 7, respectively, and in some cases at least about 10 and 8, respectively. In some embodiments, the scleral lens solutions is considered free of strong divalent metal ions chelators if the concentration of such chelators in the solution is such that the strong chelator bind less than 1 percent, and in some embodiments less than 0.1 percent, of the total calcium and magnesium present in the solution.

In some embodiments, to reduce edema formation and promote corneal health and healing, the scleral lens solution is provided to have an osmolality equal to or greater that of the corneal tissue or normal tears, or in some cases, diseased or compromised corneal tissue. In some cases, the scleral lens solutions has an osmolality greater that of the corneal tissue. This can advantageously promote the transport of metabolic waste products from the corneal tissue into the scleral lens solution, which in turn, is thought to promote tissue healing. In some embodiments, the osmolality of the scleral lens solution is provided to have a range of about 300 to about 450 milliosmols (mosm), and in some cases, about 310 to about 380 mosm, and in some cases, about 330 to about 350 mosm, and in some cases, between 330 and 350 mosm, and in some cases, about 340 mosm.

Additionally, to reduce edema formation and promote healing, embodiments of the scleral lens solutions can have a balance of these cations that is similar to that thought to exist in corneal tissue or normal tears. In some embodiments, the sodium concentration in the solution is in a range of about 120 to about 170 millimoles per liter (mM), and in some embodiments more preferably, about 145 to 155 mM. In some embodiments, the potassium concentration in the solution is in a range of about 6 to about 42 mM, and in some embodiments more preferably, about 20 to 30 mM. In some embodiments, the calcium concentration in the solution is in a range of about 0.5 to about 2.5 mM, and in some embodiments more preferably, about 1.2 to 1.8 mM. In some embodiments, the magnesium concentration in the solution is in a range of about 0.3 to about 1.7 mM, and in some embodiments more preferably, about 0.8 to 1.2 mM. Embodiments of the aqueous solution includes all combinations of these concentrations ranges of the four cations and osmolality range.

In some embodiments, to facilitate providing the desired balance of these cations, a mole ratio of sodium to potassium in the solution is in the range of about 5.0:1 to about 6.5:1, and in some cases, about 5.7:1 to about 5.9:1. Similarly, in some embodiments, a mole ratio of calcium to magnesium in the solution is in the range of about 1:1 to about 2:1, and in some cases, about 1.4:1 to about 1.6:1.

In some embodiments, the solution further includes anions that provide a scleral lenses solution that exposes the corneal and other ocular tissue under the lens with an environment similar to that of normal tears. Non-limiting examples of such anions include chloride, phosphate citrate, bicarbonate or similar anions.

In some embodiments of the solution, to provide an environment similar to that of normal tears, the pH of the solution is in a range from about 6.5 to about 8.7, and in some cases, from about 7 to about 8.5, and in some cases, from about 7.1 to about 7.8, and in some cases, between 7.3 and 7.5.

To facilitate maintaining the pH in the desired pH range, the embodiments of the scleral lenses solution can include a pH buffer. In some embodiments, to counteract pH changes of the solution associated with carbon dioxide generation by ocular tissue under the lens, the buffer in the solution has a concentration in a range from 10 to 100 mM.

The buffer is selected for its compatibility with living corneal and other ocular tissue. In some embodiments, for example, the buffer includes a phosphate buffer having a concentration in a range of 25 to 35 mM. For instance, in some embodiments, the buffer includes, or is, sodium Phosphate having a concentration of about 0.35 grams per 100 milliliter (mL) of solution or 0.35 wt %/volume or about 29 mM. For example, in some embodiments the buffer includes, or is, a borate buffer in a having a concentration in a range of about 70 to 80 mM. For instance, in some embodiments, the buffer includes, or is, sodium borate and boric acid having concentration of about 0.05 grams and 0.5 gm per 100 mL of solution, respectively, or 0.05 to 0.5 wt %/volume, respectively, or a about 1.3 and 79 mM, respectively.

In some embodiments, the scleral lens solution can include other buffer components such as weak acids and bases, e.g., in concentrations ranging from about 1 to about 50 mM, in some embodiments. Non-limiting examples include citrate, bicarbonate, or acetate, or, various combinations of such buffers.

In some embodiments, the scleral lenses solution includes cations consisting essentially of sodium, potassium, calcium and magnesium. That is, in such embodiments, cations other than sodium, potassium, calcium and magnesium are only present in trace amounts, e.g., in some cases, less than about 0.010 mM, and in some cases, less than about 0.0010 mM, and in some cases, less than about 0.00010 mM.

In some embodiments of the scleral lens solution, however, in addition to sodium, potassium, calcium and magnesium the solution can further include zinc, copper and in some cases both zinc and copper. While not being limited by theoretical considerations, it is thought to be advantageous to provide zinc and/or copper in sufficient concentrations to facilitate certain metalloenzymes to have normal enzymatic activity, and that the activation of such metalloenzymes is thought to promote healing of corneal tissue. In some embodiments, the zinc concentration in the solution is in a range of about 18 to about 42 mg/l, and in some cases, about 25 to about 35 mg/l. In some embodiments, the copper concentration in the solution is in a range of about 0.03 to about 0.1 mg/l, and in some cases, about 0.6 to about 0.8 mg/liter.

In some such embodiments, the scleral lenses solution includes cations that consists essentially of sodium, potassium, calcium, magnesium, zinc and copper. That is, in such embodiments, cations other than sodium, potassium, calcium, magnesium, zinc and copper are only present in trace amounts, e.g., in some cases, less than about 0.010 mM, and in some cases less than about 0.0010 mM, and in some cases, less than about 0.00010 mM.

Some embodiments of the scleral lenses solution can further include one or more monosaccharides. While not being limited by theoretical considerations, it is thought that monosaccharides can provide a source of energy for the corneal tissue, which is thought to promote healing. The monosaccharide are advantageously easily absorbed into corneal tissue, e.g., more easily absorbed as compared to disaccharides or more complex saccharides. Non-limiting example monosaccharides include glucose, mannose, galactose, sorbitol, mannose or combinations thereof. In some embodiments, the total monosaccharide concentration in the solution is in a range of about 10 to about 100 mg/liter, and in some cases, about 10 to about 60 mg/l.

Some embodiments of the scleral lenses solution can further include a demulcent. The demulcent facilitates relieving irritation of the corneal tissue or other occular tissue in contact with the scleral lens. Non-limiting example demulcents include hydroxypropylmethyl cellulose (HPMC) or compounds familiar to one skilled in the pertinent art. In some embodiments, the total demulcent concentration in the solution is in a range of about 0.1 to about 1.0 g/l, and in some cases, about 0.2 to about 0.5 g/l.

Some embodiments of the scleral lenses solution can further include a reducing agent. The reducing agent can facilitate normal function and health of the corneal tissue. The reducing agent can also facilitate easing discomfort associated with inserting scleral lens over the cornea and maintaining the post-lens tear film. Non-limiting example reducing agents include reduced glutathione, glutathione, lactate, adenosine or combinations thereof. In some embodiments, the total reducing agent concentration in the solution is in a range of about 0.1 to about 0.5 mg/l, and in some cases, about 0.3 to about 0.5 mg/l.

In some embodiments, the scleral lenses solution is substantially free of artificial preservatives. The term substantially free as used herein refers to a preservatives concentration in the scleral lenses solution that is lower than the minimum concentration for biocidal activity. Artificial preservatives are often added to conventional lens solution to reduce or delay microorganism growth. Non-limited examples of such preservatives include benzalkonium chloride, chlorhexidine acetate or gluconate, thiomersal or similar organomercury compounds, or other ophthalmic preservatives having bactericidal, microbicidal, antifungal, antiseptic or other biocidal activities.

For some embodiments of the disclosed scleral lenses solution, however, the benefits of such preservatives embodiments are out-weighed by concerns that the preservative could be toxic to or at least delay the healing of diseased or compromised corneal tissue. An additional benefit in not including such artificial preservatives avoiding potential allergic reactions that may be caused by such preservatives in some individuals.

Still another embodiment of the disclosure is a method of preparing a scleral lens solution (e.g., a scleral lens insertion, rewetting or rinse solution). FIG. 1 illustrates by flow diagram, selected aspects of an example method 100 of preparing a scleral lenses solution according to the principles of the present disclosure. Any of the above-described embodiments of the scleral lenses solution can be prepared according to the method 100.

The method 100 comprises a step 105 of providing a volume of liquid water, e.g., a volume up to the total volume used in a batch of the solution. Non-limiting examples of the volume of water include distilled or deionized and sterilized water or other water preparations, familiar to those skilled in the pertinent arts, suitable for the manufacture of medical devices. In some embodiments the volume of water provided in step 105 equals about 70 to about 80 percent, and in some cases, percent of the total volume of water of the final (e.g., batch) scleral lens solution.

The method further comprises a step 110 of adding sodium, potassium, calcium and magnesium cations to the volume of water to form a solution, and, a step 112 of adjusting the pH of the solution in a range from about to 7 to about 8.7, e.g., using hydrochloric acid or sodium hydroxide or other suitable strong acids or bases.

In some embodiments of the method 100, as part of step 110, in step 115, salts of sodium, potassium, calcium and magnesium (e.g., chloride salts) can be added to the solution.

Various embodiments of the method 100 can further include, without limitation, any one of, or any combinations of the below-described additional steps.

Some embodiments of the method 100 further include in step 120, adding weak acids or bases to the solution. Non-limiting examples include boric acid, phosphoric acid, citric acid, acetic acid, and sodium and potassium salts of these acids as well as other soluble salts. In some cases some of the weak acids or bases added in step 120 can be part of the step 112 of adjusting the pH. In some cases, at least a portion of the anions of these acids or bases for step 120 can be introduced as salts of sodium, potassium, calcium or magnesium as part of step 115. Non-limiting examples include sodium, potassium, calcium or magnesium phosphate, sodium, potassium, calcium or magnesium borate and boric acid, sodium, potassium, calcium or magnesium bicarbonate, and/or, sodium, potassium, calcium or magnesium acetate.

In some embodiments, the method 100 can include adding zinc cations (step 130), and/or adding a copper cations (step 135), e.g., as zinc and copper salts. In some embodiments, the method 100 includes adding one or more monosaccharides (step 140), e.g. monosaccharides, such as but not limited to, glucose, mannose, or galactose, or, sugar alcohols such as sorbitol. In some embodiments, the method 100 includes adding a demulcent (step 145), e.g., such as but not limited to, hydroxypropylmethyl cellulose, and/or polyvinylpyrrolidinone. In some embodiments, the method 100 include adding a reducing agent (step 150) e.g., such as but not limited to glutathione.

In some embodiments of the method 100, any of the ingredients in steps 110-150 can be added as solid or liquid components, slurries with water or as solutions in water. For instance, one or more of these ingredients can be added as solid or liquid components, as slurries or as concentrated solutions.

In some embodiments the volume of water provided in step 105 and the subsequently formed solution in step 110 are maintained a ambient temperatures (e.g., about 20 to 22° C.). In some embodiments, in step 160, the volume of water provided in step 105 can be heated to facilitate dissolving the ingredients added to the volume of water. In some embodiments, the heating step 160 can be applied to the scleral lens solution formed in step 110 as the different additional ingredients are added. In some embodiments heating can be applied to stock solutions of the one or more individual ingredients before the ingredients are added to the scleral lens solution in steps 110-150.

In some embodiments the volume of water provided in step 105, the scleral lens solution, and/or, individual stock solution of ingredients, can be heated to a temperature of at least about 40° C., and in some cases, at least about 50° C., and in some cases, at least about 70° C., and in some cases, up to about 80° C. In some cases, the volume of water provided in step 105 can be heated in step 160 during, or before, any of the indigents described in steps 110-150 are being added. In some embodiments, for instance, to facilitate rapid dissolving, it can be advantageous to heat the solution in accordance with step 160 before calcium or magnesium are added.

Some embodiments of the method 100 can further include a step 165 of adjusting the total volume of the scleral lens solution. For instance, the volume of water added can bring the batch of the solution up to a sufficient amount (Quantum Sufficiat, QS) so that the concentrations of the ingredients are at their target values in the final (e.g., batch) scleral lens solution.

Some embodiments of the method 100 can further include a step 170 of sterilizing the scleral lens solution. Non-limiting examples of sterilizing the solution according to step 170 include one or more of heating, filtering (e.g., through a submicron filter), or exposure to ultraviolet or ionizing radiation.

Some embodiments of the method 100 can further include a step 180 of packaging the scleral lens solution. For instance, in some embodiments, step 180 can include sealing a volume of the batch scleral lens solution in a sterilized container (e.g., glass or plastic vials or bottles). In some cases, the volume packaged in step 180 corresponds to a single-use volume of less than 30 mL.

Figure 2:
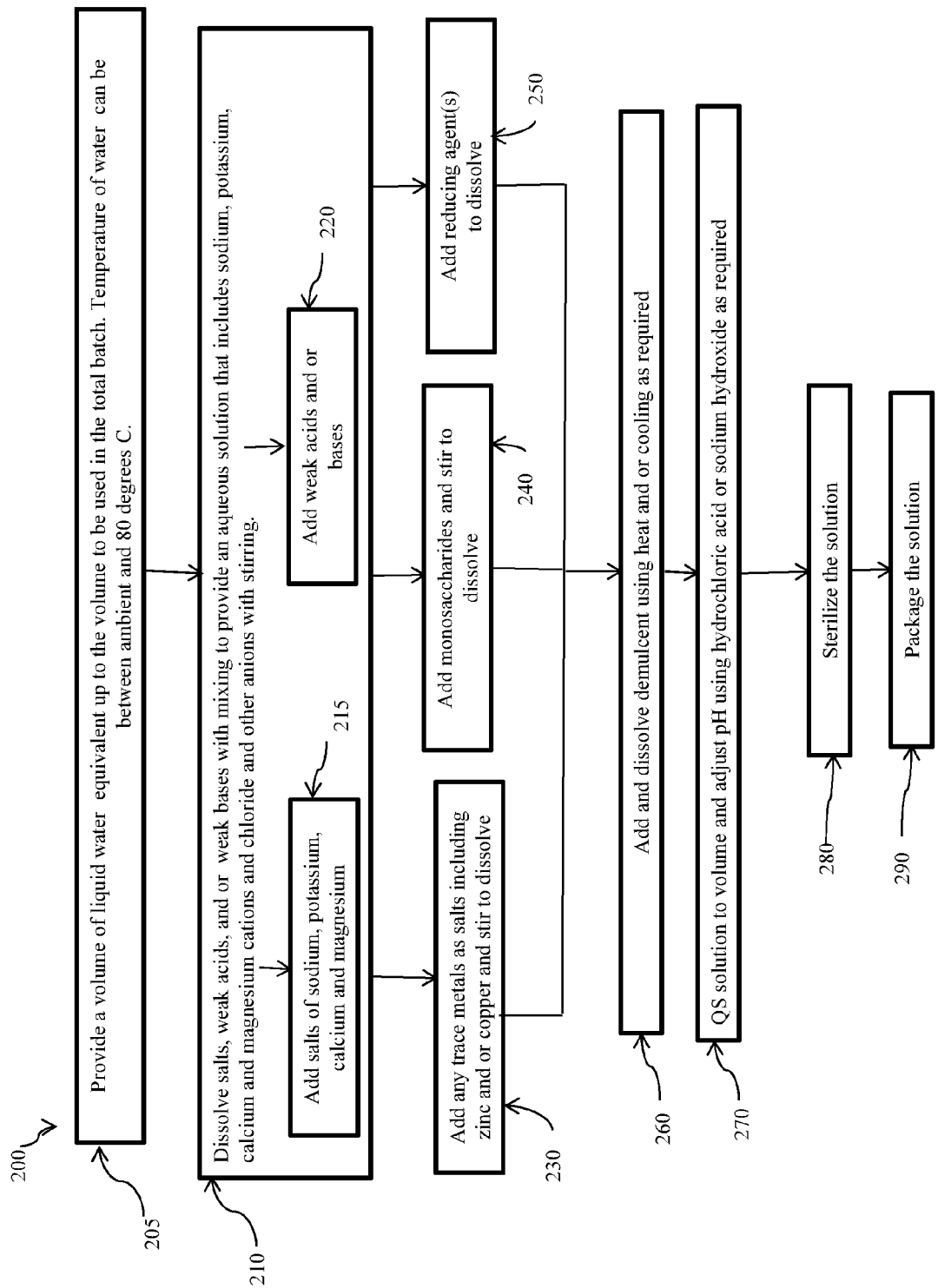
FIG. 2 illustrates by flow diagram, selected aspects of another example method of preparing a scleral lens solution according to the principles of the present disclosure.

FIG. 2 illustrates by flow diagram, selected aspect of another example method 200 of preparing a scleral lens insertion solution according to the principles of the present disclosure. Any of the above-described embodiments of the scleral lens solution can be prepared according to the method 200.

The method comprises a step 205 of providing a volume of liquid water suitable for the manufacture of medical devices. The volume of this initial step can provide in some embodiments, e.g., approximately 75% of the total volume of water used to make the solution.

In some embodiments, step 210 involves dissolving in the volume of water, the salts of sodium, potassium, calcium, and magnesium (step 215).

In some embodiments of the method 200, weak acids and or bases (step 220) can be added. Non-limiting examples include boric acid, phosphoric acid, citric acid, acetic acid, and sodium and potassium salts of these acids as well as other soluble salts.

In some embodiments zinc and copper salts can be added in step 230.

In some embodiments a monosaccharide such as but not limited to monosaccharides such as glucose, mannose, and galactose as well as sugar alcohols such as sorbitol can be added in step 240.

In some embodiments a reducing agent such as but not limited to glutathione or reduced forms can be added in step 250.

In some embodiments a demulcent such as but not limited to hydroxypropylmethyl cellulose, polyvinylpyrrolidinone, and can be added in step 260. The process for making these materials may vary and require pre-treatment.

These materials may be added as solid or liquid components, as slurries or as concentrated solutions.

In some embodiments materials included in steps 210-260 may be added as solid or liquid components, slurries with water or as solutions in water.

In some embodiments additional water can be added to bring the volume to the total required water and the pH adjusted using hydrochloric acid or sodium hydroxide or suitable strong acid in step 270.

Some embodiments of method 200 can further include a step 280 of sterilizing the solution. This can be accomplished by one or more of heating, filtering (e.g. through a submicron filter) or exposure to ultraviolet or ionizing radiation.

Some embodiments of method 200 include a step 290 of packaging the solution. For instance filling the product into sterile containers made from plastic or glass. In some cases the solution of step 290 is filled in volumes for single use and corresponds to volumes less than 10 milliliters.

Figure 3:
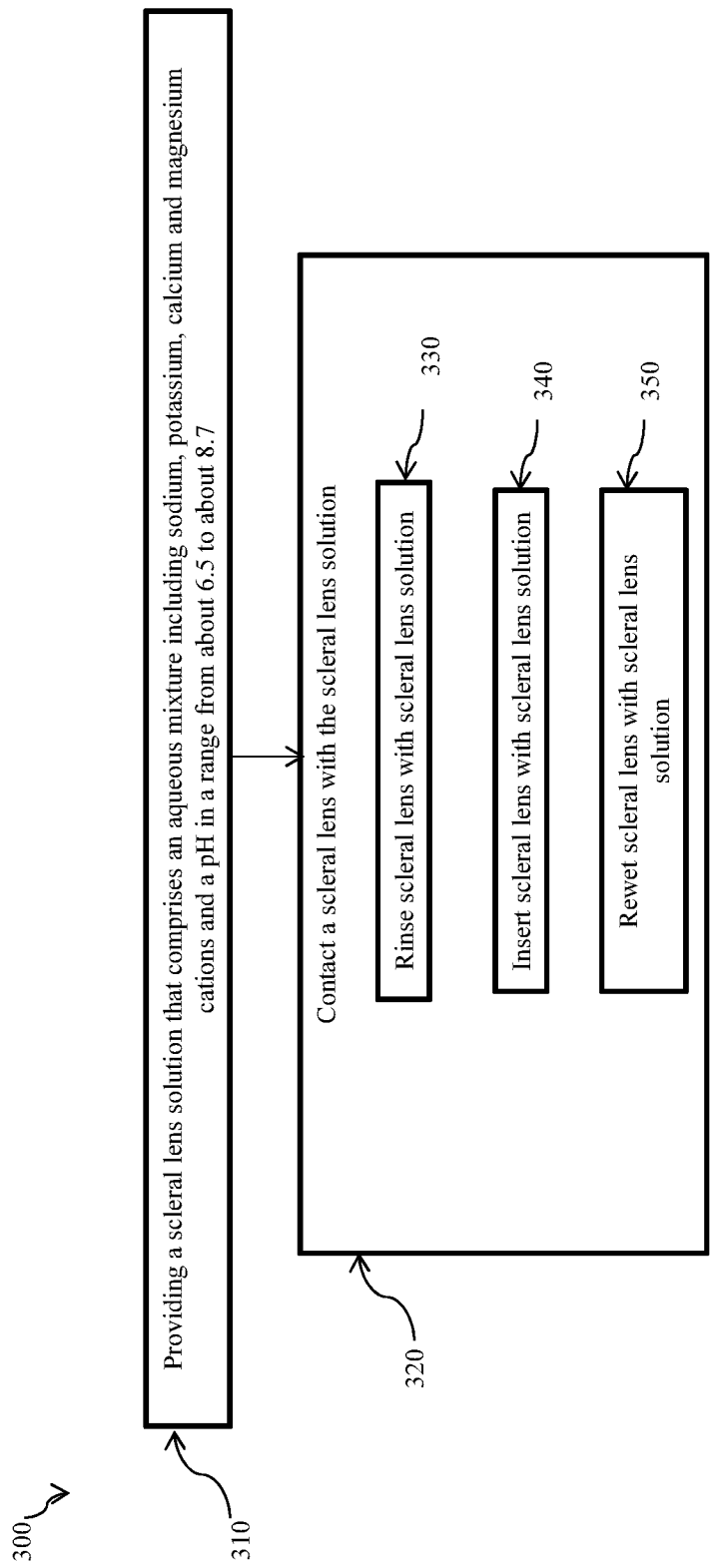
FIG. 3 illustrates by flow diagram, selected aspects of an example method of using a scleral lens solution according to the principles of the present disclosure.

Still another embodiment of the disclosure is a method using a scleral lens solution. FIG. 3 illustrates by flow diagram, selected aspects of an example method 300 of using a scleral lens solution according to the principles of the present disclosure.

The method 300 comprises a step 310 providing a scleral lens solution that comprises an aqueous mixture including sodium, potassium, calcium and magnesium cations and a pH in a range from about 6.5 to about 8.7. The method further comprises a step 320 of contacting a scleral lens with the scleral lens solution.

In some embodiments, the step 320 of contacting the scleral lens with the scleral lens solution is part of using the scleral lens solution as a rinse solution in step 330. For example in the process of caring for scleral lenses, the lenses are cleaned and disinfected using an approved cleaning and disinfecting/soaking products that contain among other ingredients disinfecting compounds, cleaners, buffers and often chelating agents. To use the scleral lens, the lenses are removed from the disinfecting soaking solution, and rinsed with the scleral lens solution in step 330 by either holding the lens in the palm of one's hand and rinsing the lens or alternatively holding the lens between the thumb and forefinger and rinsing both sides of the lens.

In some embodiments, the step 320 of contacting the scleral lens with the scleral lens solution is part of using the scleral lens solution as an insertion solution in step 340. For example, as part of step 340, the concave side of the scleral lens can be filled with one of the scleral lens solutions of the disclosure and the lens inserted in the eye such that the lens remains filled with the solution and no air bubbles are trapped between the lens and the cornea. For example in some embodiments, after rinsing (step 330), the lens is placed on the forefinger with the concave side up or alternatively using a device to hold the lens. The concave side of a lens is maintained horizontally and filled with the scleral lens solution. The lens is maintained horizontal to prevent loss of the solution and the lens is inserted into the eye maintaining the head horizontal to prevent loss of the solution from the concave portion of the lens.

In some embodiments, the step 320 of contacting the scleral lens with the scleral lens solution is part of using the scleral lens solution as a re-wetting solution in step 350.

To further illustrate various features of the disclosed scleral lens solution, several non-limiting example formulations of scleral lens solutions are presented below. In the examples to follow, the pH of the aqueous solutions was adjusted to the selected pH using solutions of sodium hydroxide and hydrochloric acid. The units in the tables are weight percent per volume (wt %/vol, e.g., grams per 100 mL of water) unless otherwise indicated.

The example solutions shown in Table 1 include phosphate buffer and various different osmolalities (e.g., by adjusting the concentration of sodium chloride) and/or pH.

TABLE 1

| Component | Example | | | |
| --- | --- | --- | --- | --- |
| | Solution 1 | Solution 2 | Solution 3 | Solution 4 |
| Sodium Chloride (wt %/vol) | 0.75 | 0.75 | 0.85 | 0.95 |
| Potassium Chloride (wt %/vol) | 0.045 | 0.045 | 0.045 | 0.045 |
| Calcium Chloride (wt %/vol) | 0.00377 | 0.00377 | 0.00377 | 0.00377 |
| Magnesium Chloride (wt %/vol) | 0.0018 | 0.0018 | 0.0018 | 0.0018 |
| Sodium Phosphate dibasic anhydrous (wt %/vol) | 0.35 | 0.35 | 0.35 | 0.35 |
| Osmolaity (mosm) | 314 | 316 | 344 | 373 |
| pH | 7.0 | 7.42 | 7.02 | 7.02 |

The example solutions shown in Table 2 include sodium borate/boric acid buffer, the demulcent (HPMC), and has various different osmolalities (e.g., by adjusting the concentration of sodium chloride and/or potassium chloride), pH, calcium or magnesium concentrations.

TABLE 2

| Component | Example | | | |
| --- | --- | --- | --- | --- |
| | Solution 5 | Solution 6 | Solution 7 | Solution 8 |
| Sodium Chloride (wt %/vol) | .7 | .7 | 0.99 | .90 |
| Potassium Chloride (wt %/vol) | 0.045 | 0.045 | 0.3129 | 0.3125 |
| Calcium Chloride (wt %/vol) | 0.00377 | 0.00377 | 0.0189 | 0.0189 |
| Magnesium Chloride (wt %/vol) | 0.0018 | 0.0018 | 0.010 | 0.010 |
| Sodium borate/boric acid (wt %/vol) | 0.052/0.5 | 0.052/0.5 | 0.052/0.5 | 0.052/0.5 |
| Osmolaity (mosm) | 314 | 316 | 344 | 373 |
| pH | 7.0 | 7.42 | 7.02 | 7.02 |
| HPMC | 0.1 | 0.1 | 0.5 | 0.5 |

What is claimed is:

1. A scleral lens solution, comprising:
   an aqueous mixture that includes sodium, potassium, calcium and magnesium cations and a pH in a range from about 6.5 to about 8.7, wherein:
   the aqueous mixture is configured to fill a void between a scleral lens and a cornea for a wear period of several hours,
   free ion concentrations of the calcium and the magnesium cations in the aqueous mixture are within 1 percent of total concentrations of the calcium and the magnesium cations in the aqueous mixture, respectively, and
   the aqueous mixture is free of artificial preservatives having biocidal activity.

2. The solution as recited in claim 1, wherein the aqueous mixture is pH buffered with at least one of phosphate buffer or borate buffer.

3. The solution as recited in claim 1, wherein the aqueous mixture is free of a strong divalent metal ion chelator.

4. The solution as recited in claim 1, wherein the aqueous mixture has an osmolality in a range of about 300 to about 450 mosm.

5. The solution as recited in claim 1, wherein the aqueous mixture includes a sodium concentration in a range of about 120 to about 170 mM.

6. The solution as recited in claim 1, wherein the aqueous mixture includes a potassium concentration in a range of about 6 to about 42 mM.

7. The solution as recited in claim 1, wherein the aqueous mixture includes a calcium concentration in a range of about 0.5 to about 2.5 mM.

8. The solution as recited in claim 1, wherein the aqueous mixture has a magnesium concentration in a range of about 0.3 to about 1.7 mM.

9. The solution as recited in claim 1, wherein the aqueous mixture has an osmolality in a range of about 300 to about 450 mosm and includes:
   a sodium concentration in a range of about 120 to about 170 mM;
   a potassium concentration in a range of about 6 to about 42 mM;
   a calcium concentration in a range of about 0.5 to about 2.5 mM; and
   a magnesium concentration in a range of about 0.3 to about 1.7 mM.

10. The solution as recited in claim 1, wherein the aqueous mixture includes sodium and potassium with a mole ratio in a range of about 5.0:1 to about 6.5:1.

11. The solution as recited in claim 1, wherein the aqueous mixture includes calcium and magnesium with a mole ratio in a range of about 1:1 to about 2:1.

12. The solution as recited in claim 1, wherein the aqueous mixture is free of a strong divalent metal ion chelator and the aqueous mixture further includes at least one of zinc in a concentration range of about 25 to about 35 mg/l or copper in a concentration range of about 0.03 to about 0.1 mg/l.

13. The solution as recited in claim 1, wherein the aqueous mixture has cations that consist essentially of sodium, potassium, calcium, magnesium, zinc and copper, the aqueous mixture is free of a strong divalent metal ion chelator, and the zinc is in a concentration range of about 25 to about 35 mg/l and the copper is in a concentration range of about 0.03 to about 0.1 mg/l.

14. The solution as recited in claim 1, wherein the aqueous mixture has cations that consists essentially of sodium, potassium, calcium, magnesium and at least one of zinc and copper.

15. The solution as recited in claim 1, wherein the aqueous mixture further includes one or more monosaccharide.

16. The solution as recited in claim 1, wherein a total concentration of the monosaccharides in the aqueous solution is in a range of about 10 to about 100 mg/liter.

17. The solution as recited in claim 1, wherein the aqueous mixture further includes one or more demulcent.

18. The solution as recited in claim 1, wherein the aqueous mixture further includes one or more reducing agent.

19. A method of preparing a scleral lens solution, comprising:
   providing a volume of liquid water; and
   adding sodium, potassium, calcium and magnesium cations to the volume of water to form a solution and adjusting the pH of the solution in a range from about 6.5 to about 8.7 to form an aqueous mixture, wherein:
   the aqueous mixture is configured to fill a void between a scleral lens and a cornea for a wear period of several hours,
   free ion concentrations of the calcium and the magnesium cations in the aqueous mixture are within 1 percent of total concentrations of the calcium and the magnesium cations in the aqueous mixture, respectively, and
   the aqueous mixture is free of artificial preservatives having biocidal activity.

20. A method using a scleral lens solution, comprising:
   providing a scleral lens solution that comprises an aqueous mixture including sodium, potassium, calcium and magnesium cations and a pH in a range from about 6.5 to about 8.7;
   contacting a scleral lens with the scleral lens solution, wherein:
   the aqueous mixture is configured to fill a void between the scleral lens and a cornea for a wear period of several hours,
   free ion concentrations of the calcium and the magnesium cations in the aqueous mixture are within 1 percent of total concentrations of the calcium and the magnesium cations in the aqueous mixture, respectively, and
   the aqueous mixture is free of artificial preservatives having biocidal activity.

21. The method as recited in claim 19, wherein the aqueous mixture is free of a strong divalent metal ion chelator.

22. The method as recited in claim 20, wherein the aqueous mixture is free of a strong divalent metal ion chelator.

* * * * *

UNITED STATES PATENT AND TRADEMARK OFFICE
CERTIFICATE OF CORRECTION

| | | |
|---|---|---|
| PATENT NO. | : 9,259,437 B2 | |
| APPLICATION NO. | : 14/284575 | |
| DATED | : February 16, 2016 | |
| INVENTOR(S) | : Ralph P. Stone | |

It is certified that error appears in the above-identified patent and that said Letters Patent is hereby corrected as shown below:

IN THE SPECIFICATION

In column 1, line 47, after --about 6 to about-- insert the number --42--

In column 6, line 34, after --cases,-- insert the number --75--

Signed and Sealed this
Third Day of May, 2016

Michelle K. Lee
*Director of the United States Patent and Trademark Office*